[12] United States Patent
Matsui et al.

(10) Patent No.: US 9,545,205 B2
(45) Date of Patent: Jan. 17, 2017

(54) DOZING PREVENTION METHOD, AND DOZING PREVENTION DEVICE (71) Applicant: UNION TOOL CO., Tokyo (JP)

(72) Inventors: Mariko Matsui, Osaka (JP); Sonoko Ishimaru, Shiga (JP); Ryo Shinozaki, Niigata (JP); Naoki Jinbo, Niigata (JP)

(73) Assignee: UNION TOOL CO., Tokyo (JP)

( * ) Notice: Subject to any disclaimer, the term of this patent is extended or adjusted under 35 U.S.C. 154(b) by 0 days.

(21) Appl. No.: 14/771,032

(22) PCT Filed: Feb. 28, 2014

(86) PCT No.: PCT/JP2014/055102
§ 371 (c)(1),
(2) Date: Aug. 27, 2015

(87) PCT Pub. No.: WO2014/133142
PCT Pub. Date: Sep. 4, 2014

(65) Prior Publication Data
US 2016/0000343 A1    Jan. 7, 2016

(30) Foreign Application Priority Data
Mar. 1, 2013    (JP) ................. 2013-041267

(51) Int. Cl.
G08B 23/00    (2006.01)
A61B 5/0245   (2006.01)
(Continued)

(52) U.S. Cl.
CPC ......... *A61B 5/02455* (2013.01); *A61B 5/0245* (2013.01); *A61B 5/16* (2013.01);
(Continued)

(58) Field of Classification Search
CPC ......... A61B 5/18; A61B 5/024; A61B 5/0245; A61B 5/02455; G08B 21/06; B60W 2040/0827
(Continued)

(56) References Cited

U.S. PATENT DOCUMENTS 5,769,085 A * 6/1998 Kawakami ............. A61B 5/024
                                                  600/519
5,941,837 A * 8/1999 Amano .................. A61B 5/024
                                                  600/503
(Continued)

FOREIGN PATENT DOCUMENTS

EP    2 138 989    12/2009
JP    6-292661     10/1994
(Continued)

OTHER PUBLICATIONS

International Search Report issued Apr. 15, 2014 in International Application No. PCT/JP2014/055102.
(Continued)

*Primary Examiner* — John A Tweel, Jr.
(74) *Attorney, Agent, or Firm* — Wenderoth, Lind & Ponack, L.L.P.

(57) ABSTRACT

A method for preventing dozing off, comprising the steps of: a measurement step measuring human heartbeats; a decision step (S4 to S8) generating a trigger, hereinafter referred to as a "drowsiness trigger", for indicating occurrence of drowsiness when a state in which a time interval between adjacent heartbeats, hereinafter referred to as a "heartbeat interval", is longer than the previous heartbeat interval consecutively occurs; and a warning step (S9) giving a warning to prevent dozing off when the drowsiness trigger is generated.

20 Claims, 10 Drawing Sheets (51) Int. Cl.
- *G08B 21/06* (2006.01)
- *A61B 5/16* (2006.01)
- *A61B 5/00* (2006.01)
- *B60K 28/04* (2006.01)
- *A61B 5/18* (2006.01)
- *B60W 40/08* (2012.01)

(52) U.S. Cl.
CPC .............. *A61B 5/18* (2013.01); *A61B 5/4812* (2013.01); *B60K 28/04* (2013.01); *B60W 40/08* (2013.01); *G08B 21/06* (2013.01); *A61B 2503/22* (2013.01); *B60W 2040/0827* (2013.01)

(58) Field of Classification Search
USPC .................................. 340/575; 600/300, 509
See application file for complete search history.

(56) References Cited

U.S. PATENT DOCUMENTS

| | | | | |
|---|---|---|---|---|
| 6,506,153 | B1* | 1/2003 | Littek | A61B 5/0205 600/500 |
| 6,575,902 | B1* | 6/2003 | Burton | G08B 21/06 340/575 |
| 7,245,960 | B2* | 7/2007 | Yasushi | A61B 5/0245 600/509 |
| 8,562,536 | B2* | 10/2013 | Osorio | A61B 5/02405 600/483 |
| 8,725,311 | B1* | 5/2014 | Breed | G08B 21/06 600/300 |
| 8,862,214 | B2* | 10/2014 | Ghodrati | A61B 5/024 600/519 |
| 9,314,181 | B2* | 4/2016 | Brockway | A61B 5/0245 |
| 2003/0199943 | A1 | 10/2003 | Katz et al. | |
| 2004/0236236 | A1* | 11/2004 | Yanagidaira | G08B 21/06 600/509 |
| 2009/0275849 | A1 | 11/2009 | Stewart | |
| 2012/0078122 | A1 | 3/2012 | Yokoyama et al. | |
| 2013/0116578 | A1* | 5/2013 | An | A61B 5/0205 600/484 |
| 2013/0237793 | A1 | 9/2013 | Farrugia et al. | |

FOREIGN PATENT DOCUMENTS

| | | |
|---|---|---|
| JP | 10-137228 | 5/1998 |
| JP | 2011-22738 | 2/2011 |
| WO | 2010/143535 | 12/2010 |
| WO | 2012/068613 | 5/2012 |

OTHER PUBLICATIONS

Rei Fukushima et al., "A method of sleepiness estimate by a correlation between RR interval and sleepiness", The Japan Society of Mechanical Engineers, No. 10-52, p. 430-433, Sep. 18, 2010.

Extended European Search Report issued Sep. 9, 2016 in European patent application No. 14 75 7488.

* cited by examiner

DOZING PREVENTION METHOD, AND DOZING PREVENTION DEVICE

TECHNICAL FIELD

The present invention relates to a method and a device for preventing dozing off, and more particularly to a technique for detecting drowsiness using a heartbeat.

BACKGROUND ART

In recent years, the number of car accidents has been decreasing. However, the number of accidents caused by health condition has been increasing. Here, the accidents caused by health condition refer to "accidents where due to drivers' diseases, the drivers were unable to continue driving their cars" (car accident reporting rules, Article 2, Item 9). The drivers' diseases in the accidents caused by health condition mainly include a myocardial infarction, a subarachnoid hemorrhage, a cerebral hemorrhage, a stroke, a heart failure, etc., and only brain and heart diseases form a majority. When drivers suffer from such diseases during driving, it inevitably leads to serious accidents and thus complete health care is strongly demanded.

In addition, about 15% of the accidents caused by health condition are accidents caused by dozing at the wheel. As with the case in which drivers suffer from a brain disease or a heart disease during driving, dozing at the wheel is highly likely to lead to serious accidents. Thus, various methods for preventing dozing at the wheel are studied. Specifically, there are, for example, a method in which driver's physical information such as a heartbeat and respiration is detected by a sensor mounted in a car and the physical information is analyzed to detect driver's drowsiness, and a method in which a driver's face image is photographed by a camera and dozing off is detected from eyelid condition, etc. For example, a "dozing prevention warning device that senses a moment of a person going into a dozing state, from his/her brainwave frequency or heart rate and gives a warning" is disclosed in Patent Document 1 (Abstract). In addition, for example, a "driver's state estimation device that detects driver's heart beat intervals and estimates a driver's state based on whether there is a change in the beat intervals" is disclosed in Patent Document 2 (Abstract).

PRIOR ART DOCUMENT

Patent Document

Patent Document 1: Japanese Unexamined Patent Application Publication No. 06-292661
Patent Document 2: Japanese Unexamined Patent Application Publication No. 2011-22738

SUMMARY OF THE INVENTION

Problems to be Solved by the Invention

In a method of detecting a brainwave frequency as in Patent Document 1, since a lot of sensors need to be attached to the head, it is not convenient to use. Also, since a brainwave is a very weak current, there is a problem that the brainwave is susceptible to disturbance noise.

In addition, as described in Patent Documents 1 and 2, it is conventionally known that a dozing state is detectable from heart rate, using the fact that heart rate decreases when falling asleep. However, detecting a decrease in heart rate and then giving a warning after a person goes into a dozing state is already too late. To prevent dozing at the wheel, there is a need to detect a pre-dozing state where a driver is about to go into a dozing state, and give a warning before going into the dozing state. In view of this, to detect the pre-dozing state, a device is produced experimentally that detects the start of decrease in heart rate and gives a warning. However, the device has a problem that, even when a person is not drowsy, the device frequently gives a warning due to erroneous detection of drowsiness and thus the person is annoyed and accordingly the device is not good.

The present invention is made in consideration of conventional problems such as those described above, and an object of the present invention is to provide a dozing prevention method and a dozing prevention device that are capable of detecting a pre-dozing state where a driver is about to go into a dozing state, while suppressing erroneous detection.

The method for preventing dozing off according to the present invention comprises the steps of a measurement step measuring human heartbeats; a decision step generating a trigger, hereinafter referred to as a "drowsiness trigger", for indicating occurrence of drowsiness when a state in which a time interval between adjacent heartbeats, hereinafter referred to as a "heartbeat interval", is longer than the previous heartbeat interval consecutively occurs; and a warning step giving a warning to prevent dozing off when the drowsiness trigger is generated.

In the decision step, it is preferred that the drowsiness trigger is generated when the state in which the heartbeat interval is longer consecutively occurs not less than four times.

In the decision step, it is preferred that the drowsiness trigger is generated when the state in which the heartbeat interval is longer consecutively occurs and a difference between the first heartbeat interval and the last heartbeat interval in the predetermined number of times exceeds a predetermined time.

Here, the predetermined time is preferably not less than 60 ms. Here, it is preferred that a R-R interval which is an interval between R waves in an electrocardiographic signal is used as the heartbeat interval.

In the decision step, it is preferred that the heartbeat interval is considered to have an abnormal value when the heartbeat interval is out of a predetermined range, the abnormal value is eliminated from a target of decision made as to whether a state in which a heartbeat interval is longer has occurred.

Here, the predetermined range is preferably 200 ms to 3000 ms.

In the decision step, it is preferred that an instantaneous heart rate is calculated by multiplying an inverse of a heartbeat interval, units of seconds, by 60; an average of instantaneous heart rates at a plurality of recent points where an absolute value of the difference between an instantaneous heart rate and the previous instantaneous heart rate is not more than a first predetermined number is calculated; the heartbeat interval is considered to have an abnormal value when an absolute value of the difference between the average and an instantaneous heart rate corresponding to a heartbeat which is an evaluation target is not less than a second predetermined number, and the abnormal value is eliminated from a target of decision made as to whether a state in which an heartbeat interval is longer has occurred.

Here, it is preferred that the first predetermined number is 30, the second predetermined number is 50, the number of a plurality of recent points is from 4 to 20.

The dozing prevention device according to the present invention is characterized in that the device accepts a heartbeat interval, decides that drowsiness has occurred when a state in which the heartbeat interval is longer than the previous heartbeat interval consecutively occurs, and gives a warning to prevent dozing off.

It is preferred that the dozing prevention device further comprises a measurement part that measures human heartbeats; and a signal processing part that generates a heartbeat interval, based on the measured human heartbeats.

Here, it is preferred that a R-R interval which is an interval between R waves in an electrocardiographic signal is used as the heartbeat interval.

Effect of the Invention

According to the dozing prevention method and the dozing prevention device according to the present invention, when a state in which a time interval between adjacent heartbeats is wider consecutively occurs, it is decided that drowsiness has occurred, and thus, a warning to prevent dozing off can be given. Accordingly, before going into a dozing state, human drowsiness is relieved and thus dozing off can be prevented, and erroneous detection can be reduced.

DESCRIPTION OF PREFERRED EMBODIMENTS

The method for preventing dozing off according to the present invention comprises the steps of a measurement step measuring human heartbeats; a decision step generating a trigger for indicating occurrence of drowsiness when a state in which a time interval between adjacent heartbeats is longer than the previous heartbeat interval consecutively occurs; and a warning step giving a warning to prevent dozing off when the drowsiness trigger is generated.

In the measurement step, a heartbeat is measured by measuring the pulse, electrocardiogram, etc., of a human (e.g., a driver of an automobile) using a pulse sensor, an electrocardiograph, etc., and the heartbeat itself is outputted or a heartbeat interval is calculated and outputted.

In the decision step, when a signal indicating a heartbeat itself is received in real time from the measurement step, a heartbeat interval is calculated based on the heartbeat signal. In addition, in the decision step, when a heartbeat interval which is calculated in the decision step or is directly outputted from the measurement step is longer than the previous heartbeat interval, a decision as to whether the heartbeat interval is longer is repeated in the same manner for a subsequent heartbeat interval, too. When a state in which the heartbeat interval is longer consecutively occurs a predetermined number of times, a drowsiness trigger is generated.

In the warning step, when a drowsiness trigger is generated in the decision step, in response to this, a warning to prevent dozing off is given. Here, the warning is, for example, a warning sound, voice that calls attention, image display that calls attention, vibration, light, and the like, and may be any warning as long as human drowsiness is relieved or the effect of preventing dozing off can be expected by the warning.

The dozing prevention device according to the present invention is characterized in that the device accepts a heartbeat interval, the device decides that drowsiness has occurred when a state in which the heartbeat interval is longer than the previous heartbeat interval consecutively occurs, and gives a warning to prevent dozing off. Here, the dozing prevention device is an analysis device that performs the above-described decision step and the above-described warning step.

As such, according to the dozing prevention method and the dozing prevention device according to the present invention, when a state in which a time interval between adjacent heartbeats is longer consecutively occurs, it is decided that drowsiness has occurred, and thus, a warning to prevent dozing off can be given. Accordingly, before going into a dozing state, human drowsiness is relieved and thus dozing off can be prevented, and erroneous detection can be reduced.

In addition, it is preferred that the dozing prevention device further comprises a measurement part that measures human heartbeats; and a signal processing part that generates a heartbeat interval, based on the measured human heartbeats.

The measurement part is a pulse sensor, an electrocardiograph, etc., that measure human heartbeats.

The signal processing part is a computer having installed thereon software that calculates a heartbeat interval based on a human heartbeat measured by the measurement part, a measuring device, etc.

When a pulse is measured using a pulse sensor in the measurement part, a human fingertip, earlobe, or the like, is irradiated with near infrared rays having a wavelength of 700 nm to 1200 nm, and the amount of reflection of the near infrared rays can be measured in a contact or contactless manner.

In addition, when an electrocardiographic signal is measured using an electrocardiograph in the measurement part, it is preferred to use, as a heartbeat interval, an R-R interval (hereinafter, described as an "RRI") which is an interval between adjacent R waves (peaks) in an electrocardiogram.
(First Embodiment)

Figure 1:
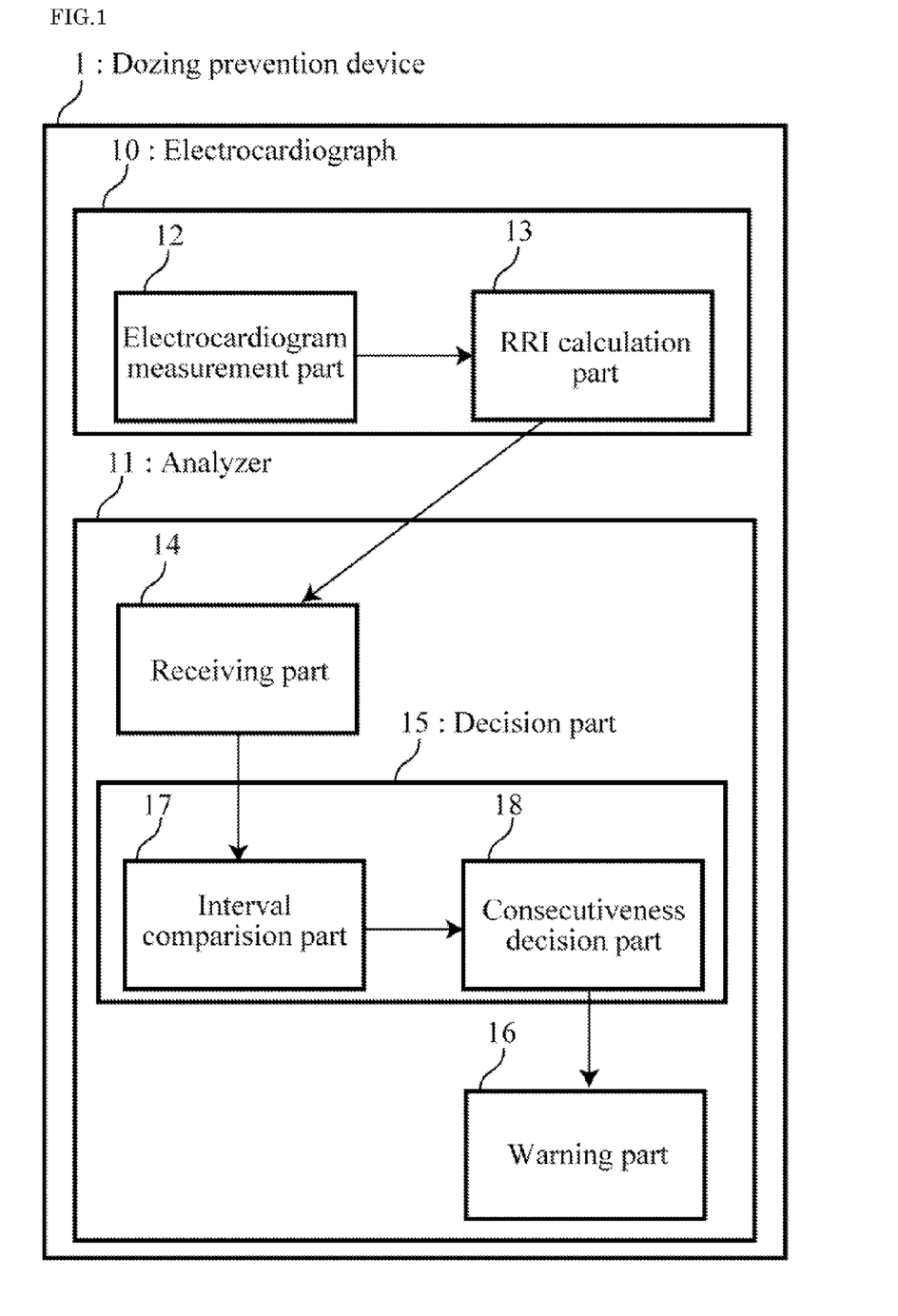
FIG. 1 is a schematic diagram showing a configuration of a dozing prevention device according to a first embodiment of the present invention.

FIG. 1 is a schematic diagram showing a configuration of a dozing prevention device according to a first embodiment of the present invention.

A dozing prevention device 1 shown in FIG. 1 comprises an electrocardiograph 10 and an analyzer 11.

The electrocardiograph 10 comprises an electrocardiogram measurement part 12 having the function of the above-described measurement part; and an RRI calculation part 13 having the function of the above-described signal processing part. The electrocardiograph 10 is compact and lightweight, and a whole main body thereof can be attached to human skin with an electrode (not shown) on the back side of the main body adhered tightly to the human chest. Thus, the electrocardiograph 10 is covered under clothing and thus is unnoticeable. The electrocardiogram measurement part 12 measures an electrocardiographic signal, with the electrode adhered tightly to the human chest. The RRI calculation part 13 calculates an RRI based on the measured electrocardiographic signal and transmits the RRI to the analyzer 11. Here, three RRIs are wirelessly transmitted all at once to reduce the frequency of transmission and receiving, by which the life of a built-in battery (not shown) improves. Note that the RRI calculation part 13 only needs to be comprised in either one of the electrocardiograph 10 or the analyzer 11. Thus, the electrocardiograph 10 does not necessarily need to comprise the RRI calculation part 13.

In addition, instead of the electrocardiograph 10, other devices that measure heartbeats, such as a pulse sensor, may be used. Since an electrocardiographic signal exhibits explicit peaks compared to pulses, when an electrocardiograph is used, the accuracy of heartbeat intervals increases, and thus, there is an advantage that erroneous recognition is less likely to occur. On the other hand, when a pulse sensor is used, there is an advantage that the measuring device is relatively easy to attach to the body. Particularly, when a contactless measurement type is used, cumbersome attachment of the measuring device to the body is unnecessary and thus there is a possibility of the measuring device spreading widely.

The analyzer 11 comprises a receiving part 14, a decision part 15, and a warning part 16, and is mounted in an automobile, etc.

The receiving part 14 receives RRIs transmitted from the electrocardiograph 10. Here, the receiving part 14 receives and holds three RRIs all at once, and outputs the RRIs in turn from the temporally oldest one.

The decision part 15 has the function of performing the above-described decision step. The decision part 15 receives an RRI from the receiving part 14, performs analysis according to a drowsiness detection algorithm, and generates a drowsiness trigger when deciding that a condition for the occurrence of drowsiness is met.

The decision part 15 includes an interval comparison part 17 and a consecutiveness decision part 18.

The interval comparison part 17 compares an RRI which is an evaluation target with the previous RRI to decide whether a state in which the RRI which is the evaluation target is longer than the previous RRI has occurred.

When the interval comparison part 17 decides that a state in which the RRI is longer has occurred, the consecutiveness decision part 18 further decides whether this state consecutively occurs a predetermined number of times. Here, the predetermined number of times is preferably not less than four times. If less than four times, the effect of suppressing erroneous operation cannot be expected.

In the first embodiment, when the consecutiveness decision part 18 decides that the state consecutively occurs the predetermined number of times, it is decided that the condition for the occurrence of drowsiness is met, and thus, the decision part 15 generates a drowsiness trigger.

The warning part 16 has the function of performing the above-described warning step. When a drowsiness trigger is generated, the warning part 16 gives a warning to prevent dozing off.

A detail of the drowsiness detection algorithm performed by the analyzer 11 will be described below.

Figure 2:
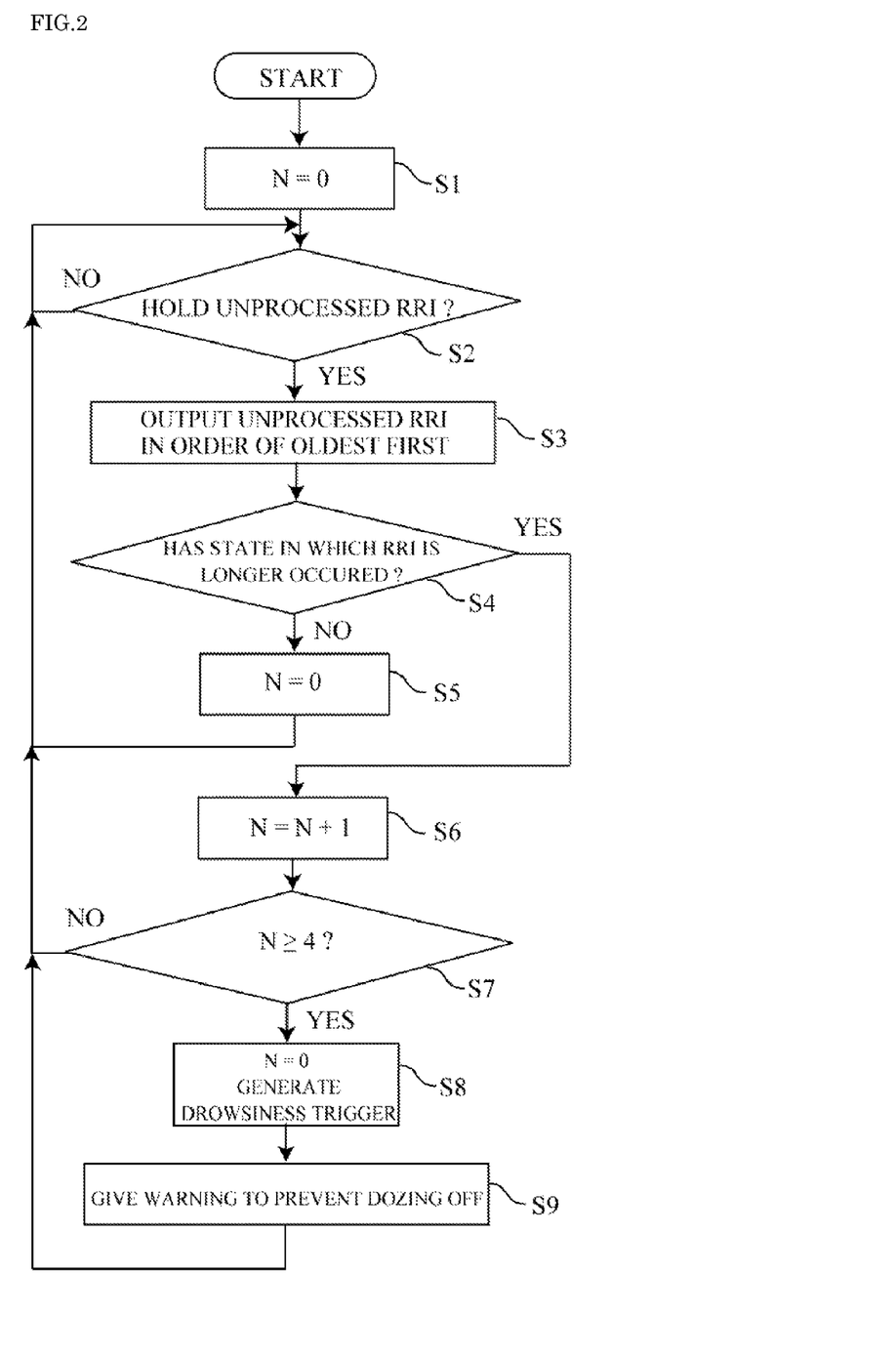
FIG. 2 is a chart showing the flow of a drowsiness detection algorithm of the first embodiment of the present invention.

FIG. 2 is a chart showing the flow of the drowsiness detection algorithm of the first embodiment of the present invention.

(1) Initial setting is performed (step S1). Here, an initial value "0" is set for a variable N indicating the number of times the state consecutively occurs.

(2) The receiving part 14 decides whether to have unprocessed RRIs (step S2).

(3) If the receiving part 14 holds unprocessed RRIs (step S2: YES), the receiving part 14 outputs the unprocessed RRIs in order of temporally oldest first (step S3).

(4) With an RRI outputted from the receiving part 14 being an evaluation target, the interval comparison part 17 compares the RRI with the previous RRI to decide whether a state in which the RRI which is the evaluation target is longer than the previous RRI has occurred (step S4).

(5) If it is decided that a state in which the RRI is longer has not occurred (step S4: NO), the variable N is set back to its initial value, and processing returns to step S2 to perform the next RRI process (step S5).

(6) If it is decided that a state in which the RRI is longer has occurred (step S4: YES), the consecutiveness decision part 18 increments the variable N (step S6).

(7) It is decided whether a predetermined number of times which is set in advance has been reached (step S7). Here, it is decided whether the variable N is not less than 4 (step S7). If the predetermined number of times which is set in advance has not been reached (step S7: NO), processing returns to step S2 to perform the next RRI process.

(8) If the predetermined number of times which is set in advance has been reached (step S7: YES), the variable N is set back to its initial value, and the decision part 15 generates a drowsiness trigger and notifies the warning part 16 of the drowsiness trigger (step S8).

(9) In response to the drowsiness trigger, the warning part 16 gives a warning to prevent dozing off (step S9).
(Second Embodiment)

Figure 3:
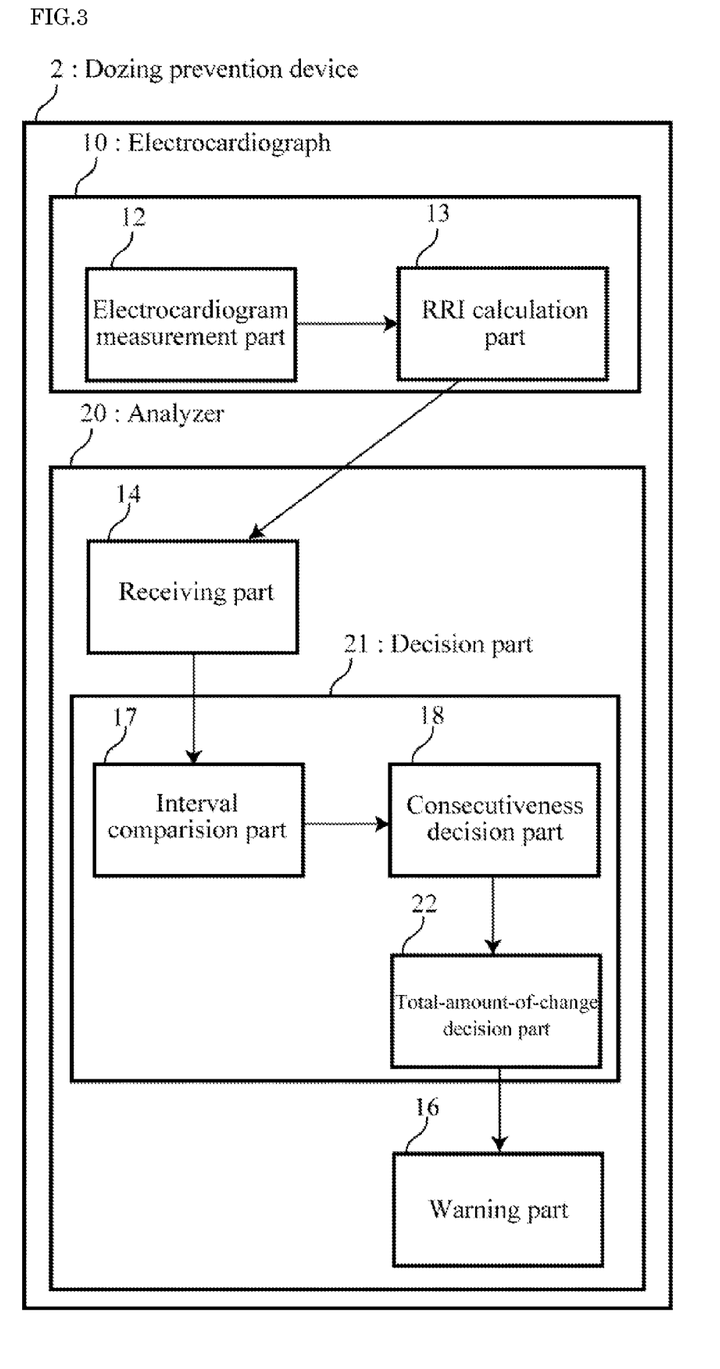
FIG. 3 is a schematic diagram showing a configuration of a dozing prevention device according to a second embodiment of the present invention.

FIG. 3 is a schematic diagram showing a configuration of a dozing prevention device according to a second embodiment of the present invention.

A dozing prevention device 2 shown in FIG. 3 comprises an electrocardiograph 10 and an analyzer 20. Note that the same components as those of the dozing prevention device 1 of the first embodiment are denoted by the same reference signs and a description thereof is omitted.

The analyzer 20 comprises a receiving part 14, a decision part 21, and a warning part 16, and is mounted in an automobile, etc., in the same manner as the analyzer 11 of the first embodiment.

The decision part 21 has the function of performing the above-described decision step. The decision part 21 receives an RRI from the receiving part 14, performs analysis according to a drowsiness detection algorithm, and generates a drowsiness trigger when deciding that conditions for the occurrence of drowsiness are met.

The decision part 21 includes an interval comparison part 17, a consecutiveness decision part 18, and a total-amount-of-change decision part 22.

When the consecutiveness decision part 18 decides that a state in which an RRI is longer consecutively occurs a predetermined number of times, the total-amount-of-change decision part 22 further decides whether the difference between the first RRI and the last RRI in the predetermined number of times exceeds a predetermined time. Here, the predetermined time is preferably not less than 60 ms, more preferably not less than 90 ms, and further more preferably not less than 120 ms. Though there is no upper limit to the predetermined time, in order to avoid analysis of a heartbeat interval with an abnormal value, the predetermined time is preferably not more than 600 ms. If the predetermined time is less than 60 ms, the effect of suppressing erroneous operation cannot be expected.

In the second embodiment, when the consecutiveness decision part 18 decides that the state consecutively occurs the predetermined number of times and the total-amount-of-change decision part 22 decides that the difference exceeds the predetermined time, it is decided that the conditions for the occurrence of drowsiness are met, and thus, the decision part 21 generates a drowsiness trigger.

A detail of the drowsiness detection algorithm performed by the analyzer 20 will be described below.

Figure 4:
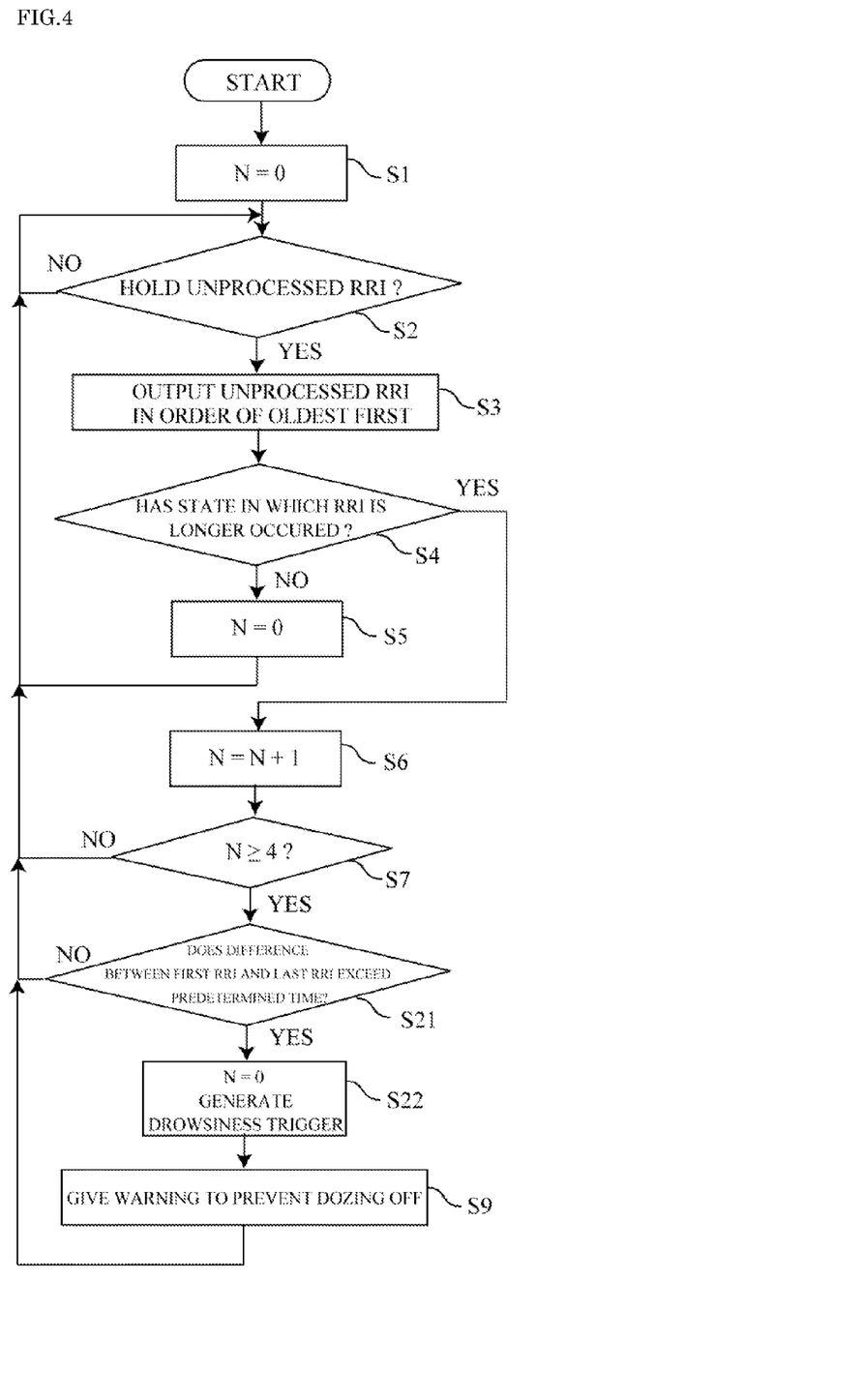
FIG. 4 is a chart showing the flow of a drowsiness detection algorithm of the second embodiment of the present invention.

FIG. 4 is a chart showing the flow of the drowsiness detection algorithm of the second embodiment of the present invention. Note that the same steps as those of the drowsiness detection algorithm performed by the analyzer 11 of the first embodiment are denoted by the same reference signs and a description thereof is omitted.

(1) to (7) The same as S1 to S7 in FIG. 2.

(8) If the predetermined number of times which is set in advance has been reached (step S7: YES), the total-amount-of-change decision part 22 decides whether the difference between the first RRI and the last RRI in the predetermined number of times exceeds a predetermined time which is set in advance (step S21). If it is decided that the difference does not exceed the predetermined time (step S21: NO), without setting the variable N back to its initial value, processing returns to step S2 to perform the next RRI process.

(9) If it is decided that the difference exceeds the predetermined time (step S21: YES), the variable N is set back to its initial value, and the decision part 21 generates a drowsiness trigger and notifies the warning part 16 of the drowsiness trigger (step S22).

(10) The same as S9 in FIG. 2.

(Third Embodiment)

Figure 5:
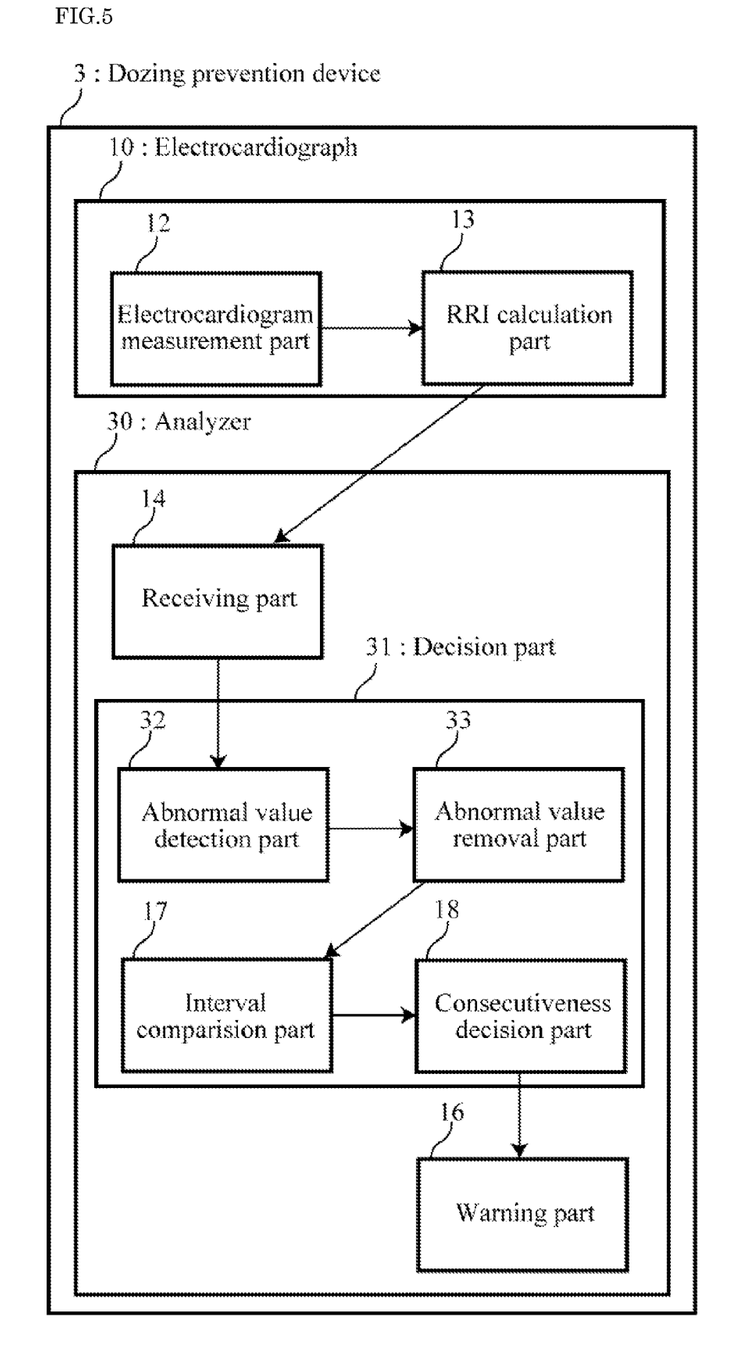
FIG. 5 is a schematic diagram showing a configuration of a dozing prevention device according to a third embodiment of the present invention.

FIG. 5 is a schematic diagram showing a configuration of a dozing prevention device according to a third embodiment of the present invention.

A dozing prevention device 3 shown in FIG. 5 comprises an electrocardiograph 10 and an analyzer 30. Note that the same components as those of the dozing prevention device 1 of the first embodiment are denoted by the same reference signs and a description thereof is omitted.

The analyzer 30 comprises a receiving part 14, a decision part 31, and a warning part 16, and is mounted in an automobile, etc., in the same manner as the analyzer 11 of the first embodiment.

The decision part 31 has the function of performing the above-described decision step. The decision part 31 receives an RRI from the receiving part 14, performs analysis according to a drowsiness detection algorithm, and generates a drowsiness trigger when deciding that a condition for the occurrence of drowsiness is met.

The decision part 31 includes an abnormal value detection part 32, an abnormal value removal part 33, an interval comparison part 17, and a consecutiveness decision part 18.

When an RRI outputted from the receiving part 14 is out of a predetermined range, the abnormal value detection part 32 considers the RRI to have an abnormal value. For example, when the RRI shows a value not more than 200 ms and when the RRI shows a value not less than 3000 ms, the values are considered to be out of the predetermined range.

The abnormal value removal part 33 eliminates an RRI which is considered by the abnormal value detection part 32 to have an abnormal value, from a target of decision made by the interval comparison part 17 as to whether a state in which an RRI is longer has occurred.

In the third embodiment, when the consecutiveness decision part 18 decides that the state consecutively occurs a predetermined number of times, it is decided that a condition for the occurrence of drowsiness is met, and thus, the decision part 31 generates a drowsiness trigger.

A detail of the drowsiness detection algorithm performed by the analyzer 30 will be described below.

Figure 6:
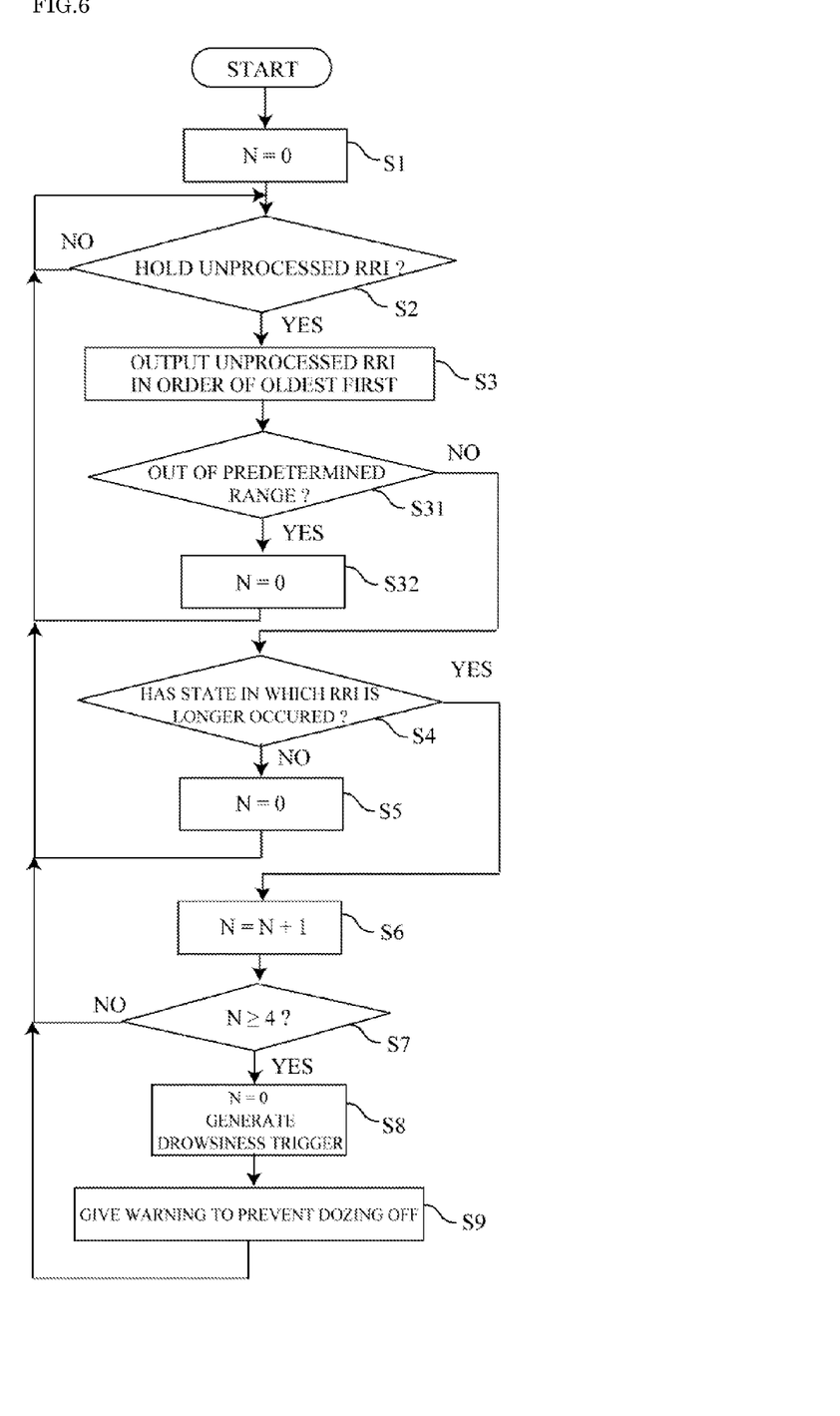
FIG. 6 is a chart showing the flow of a drowsiness detection algorithm of the third embodiment of the present invention.

FIG. 6 is a chart showing the flow of the drowsiness detection algorithm of the third embodiment of the present invention. Note that the same steps as those of the drowsiness detection algorithm performed by the analyzer 11 of the first embodiment are denoted by the same reference signs and a description thereof is omitted.

(1) to (3) The same as S1 to S3 in FIG. 2.

(4) When an RRI outputted from the receiving part 14 is out of a predetermined range, the abnormal value detection part 32 considers the RRI to have an abnormal value (step S31).

(5) If the RRI is considered to have an abnormal value (step S31: YES), the abnormal value removal part 33 sets the variable N back to its initial value, and processing returns to step S2 to perform the next RRI process (step S32).

(6) to (11) If the RRI is not considered to have an abnormal value (step S31: NO), the same as S4 to S9 in FIG. 2.

(Fourth Embodiment)

Figure 7:
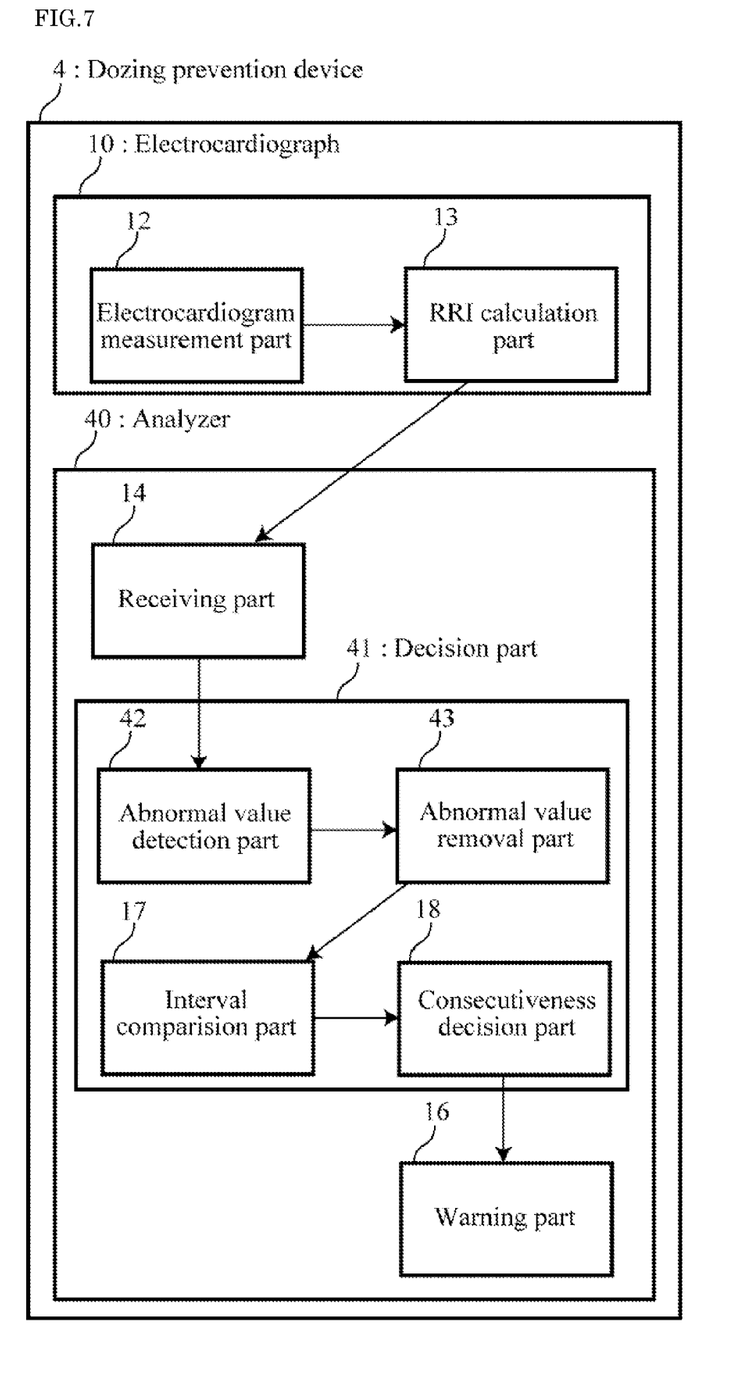
FIG. 7 is a schematic diagram showing a configuration of a dozing prevention device according to a fourth embodiment of the present invention.

FIG. 7 is a schematic diagram showing a configuration of a dozing prevention device according to a fourth embodiment of the present invention.

A dozing prevention device 4 shown in FIG. 7 comprises an electrocardiograph 10 and an analyzer 40. Note that the same components as those of the dozing prevention device 1 of the first embodiment are denoted by the same reference signs and a description thereof is omitted.

The analyzer 40 comprises a receiving part 14, a decision part 41, and a warning part 16, and is mounted in an automobile, etc., in the same manner as the analyzer 11 of the first embodiment.

The decision part 41 has the function of performing the above-described decision step. The decision part 41 receives an RRI from the receiving part 14, performs analysis according to a drowsiness detection algorithm, and generates a drowsiness trigger when deciding that a condition for the occurrence of drowsiness is met.

The decision part 41 includes an abnormal value detection part 42, an abnormal value removal part 43, an interval comparison part 17, and a consecutiveness decision part 18.

The abnormal value detection part 42 decides whether an RRI outputted from the receiving part 14 is to be considered to have an abnormal value. In the fourth embodiment, an instantaneous heart rate is calculated by multiplying an inverse of an RRI (units of seconds) by 60. An average of instantaneous heart rates at a plurality of recent points ("eight points" in the present embodiment) where an absolute value of the difference between an instantaneous heart rate and the previous instantaneous heart rate is not more than a first predetermined number ("18" in the present embodiment) is calculated. Then, when an absolute value of the difference between the average and an instantaneous heart rate corresponding to an RRI which is an evaluation target is not less than a second predetermined number ("35" in the present embodiment), the RRI which is the evaluation target is considered to have an abnormal value. Here, the first predetermined number is preferably 30, more preferably 20, and further more preferably 15. In addition the second predetermined number is preferably 50, more preferably 40, and further more preferably 30.

Note that the first predetermined number, the second predetermined number, and the number of a plurality of recent points may be changed as appropriate, according to individual differences, etc. For example, the first predetermined number may be changed as appropriate to not more than 30, the second predetermined number to not less than 30, and the number of a plurality of recent points within a range of 4 to 20.

The abnormal value removal part 43 eliminates an RRI which is considered by the abnormal value detection part 42 to have an abnormal value, from a target of decision made by the interval comparison part 17 as to whether a state in which an RRI is longer has occurred.

In the fourth embodiment, when the consecutiveness decision part 18 decides that the state consecutively occurs a predetermined number of times, it is decided that a condition for the occurrence of drowsiness is met, and thus, the decision part 41 generates a drowsiness trigger.

A detail of the drowsiness detection algorithm performed by the analyzer 40 will be described below.

Figure 8:
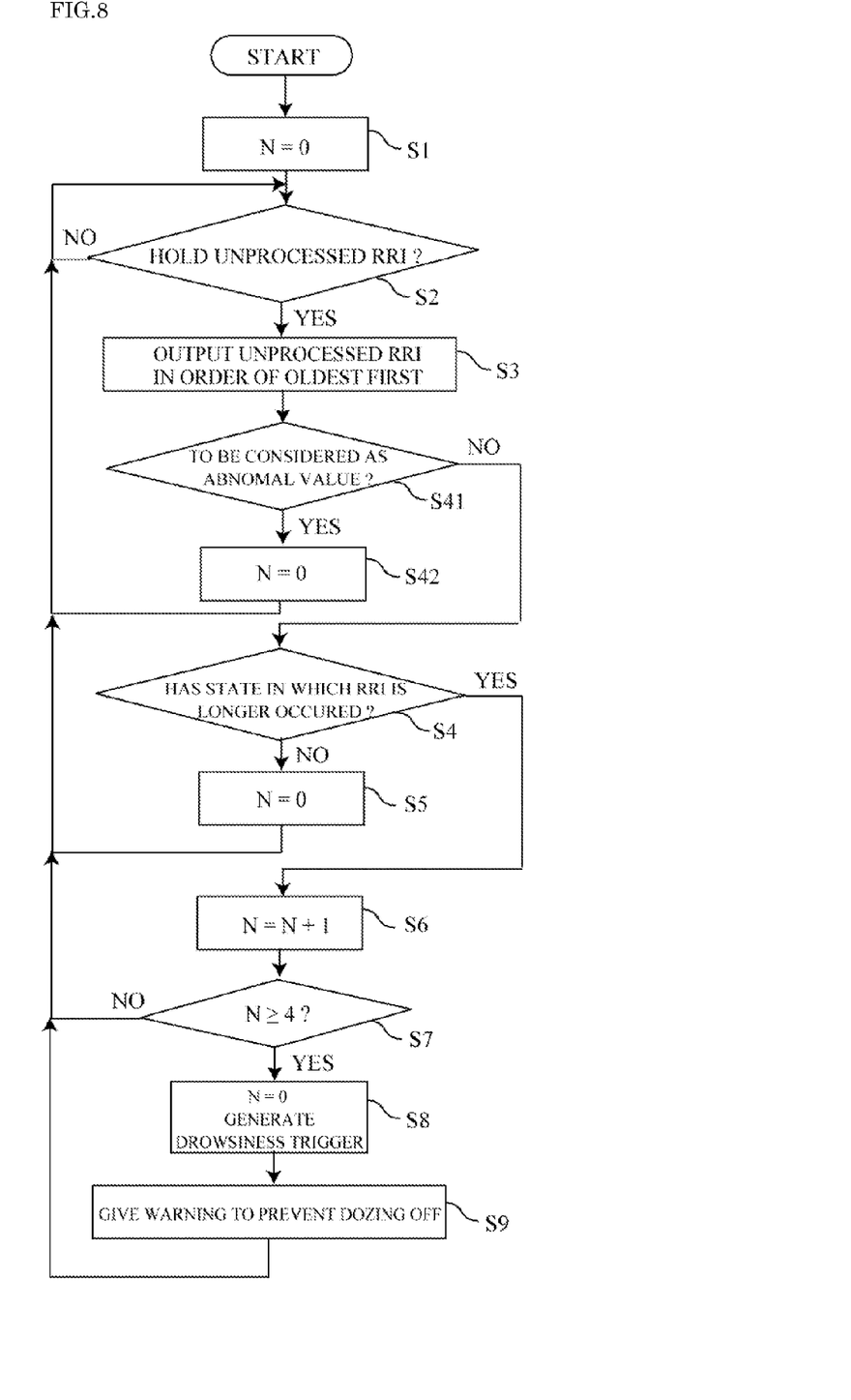
FIG. 8 is a chart showing the flow of a drowsiness detection algorithm of the fourth embodiment of the present invention.

FIG. 8 is a chart showing the flow of the drowsiness detection algorithm of the fourth embodiment of the present invention. Note that the same steps as those of the drowsiness detection algorithm performed by the analyzer 11 of the first embodiment are denoted by the same reference signs and a description thereof is omitted.

(1) to (3) The same as S1 to S3 in FIG. 2.

(4) The abnormal value detection part 42 decides whether an RRI outputted from the receiving part 14 is to be considered to have an abnormal value (step S41).

(5) If the RRI is considered to have an abnormal value (step S41: YES), the abnormal value removal part 43 sets the variable N back to its initial value, and processing returns to step S2 to perform the next RRI process (step S42).

(6) to (11) If the RRI is not considered to have an abnormal value (step S41: NO), the same as S4 to S9 in FIG. 2.

(Fifth Embodiment)

Figure 9:
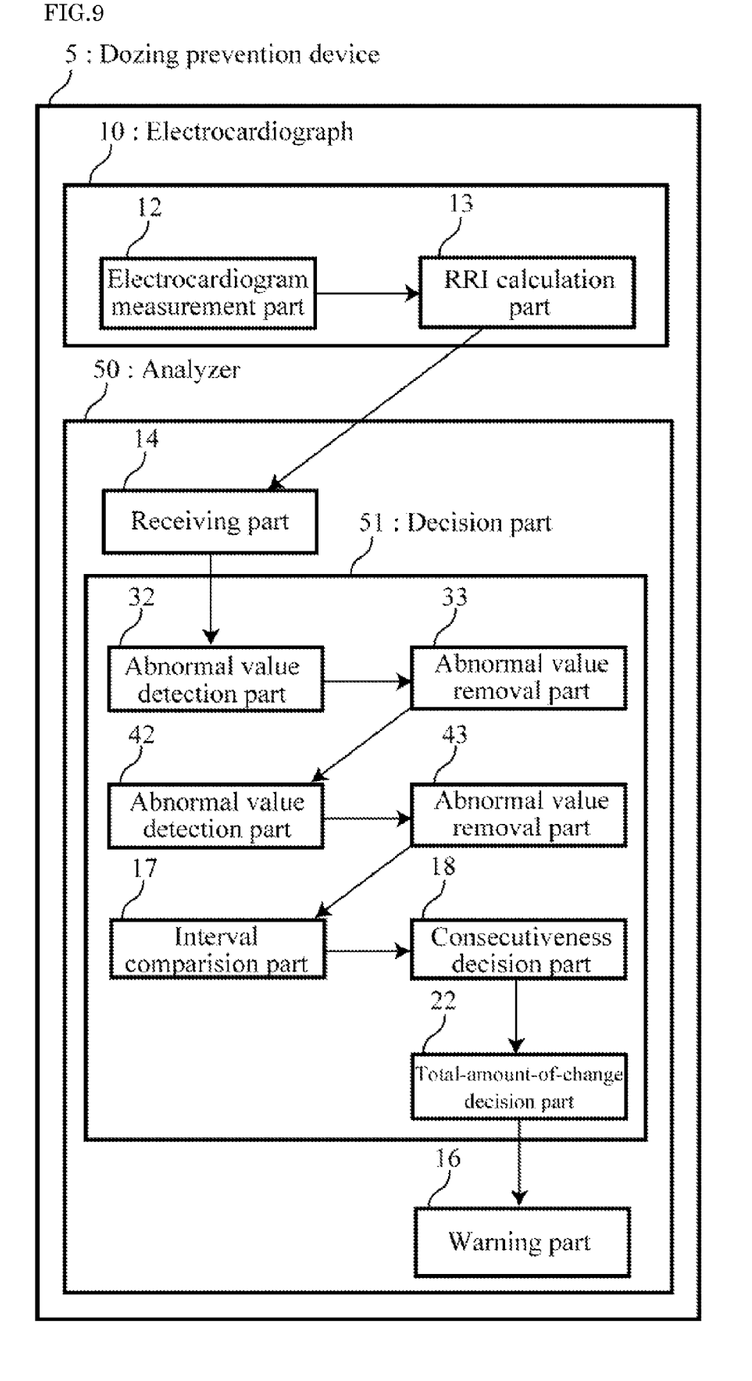
FIG. 9 is a schematic diagram showing a configuration of a dozing prevention device according to a fifth embodiment of the present invention.

FIG. 9 is a schematic diagram showing a configuration of a dozing prevention device according to a fifth embodiment of the present invention.

A dozing prevention device 5 shown in FIG. 9 comprises an electrocardiograph 10 and an analyzer 50. Note that the same components as those of the dozing prevention device 1 of the first embodiment, the dozing prevention device 2 of the second embodiment, the dozing prevention device 3 of the third embodiment, and the dozing prevention device 4 of the fourth embodiment are denoted by the same reference signs and a description thereof is omitted.

The analyzer 50 comprises a receiving part 14, a decision part 51, and a warning part 16, and is mounted in an automobile, etc., in the same manner as the analyzer 11 of the first embodiment.

The decision part 51 has the function of performing the above-described decision step. The decision part 51 receives an RRI from the receiving part 14, performs analysis according to a drowsiness detection algorithm, and generates a drowsiness trigger when deciding that conditions for the occurrence of drowsiness are met.

The decision part 51 includes an abnormal value detection part 32, an abnormal value removal part 33, an abnormal value detection part 42, an abnormal value removal part 43, an interval comparison part 17, a consecutiveness decision part 18, and a total-amount-of-change decision part 22.

A detail of the drowsiness detection algorithm performed by the analyzer 50 will be described below.

Figure 10:
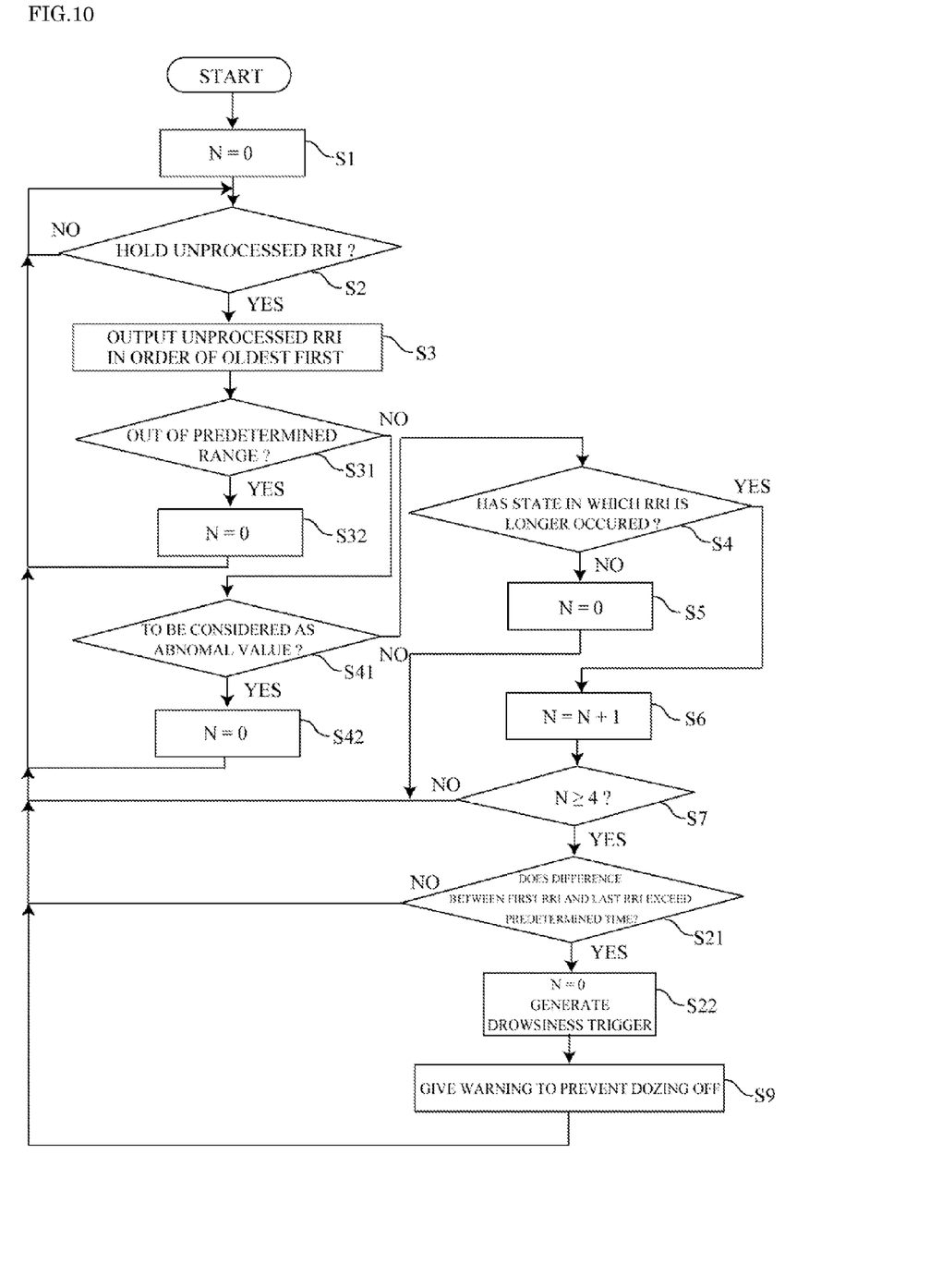
FIG. 10 is a chart showing the flow of a drowsiness detection algorithm of the fifth embodiment of the present invention.

FIG. 10 is a chart showing the flow of the drowsiness detection algorithm of the fifth embodiment of the present invention. Note that the same steps as those of the drowsiness detection algorithm performed by the analyzer 11 of the first embodiment, the analyzer 20 of the second embodiment, the analyzer 30 of the third embodiment, and the analyzer 40 of the fourth embodiment are denoted by the same reference signs and a description thereof is omitted.

(1) to (3) The same as S1 to S3 in FIG. 2.

(4) to (5) The same as S31 to S32 in FIG. 6.

(6) to (7) The same as S41 to S42 in FIG. 8.

(8) to (11) If the RRI is not considered to have an abnormal value (step S41: NO), the same as S4 to S7 in FIG. 2.

(12) to (13) The same as S21 to S22 in FIG. 4.

(14) The same as S9 in FIG. 2.

Note that the above-described embodiments can be combined together as appropriate as long as the combination does not cause a contradiction.

(Verification)

Using the dozing prevention device 5 of the fifth embodiment, verification is performed for the usefulness of the dozing prevention device of the present invention.

A compact electrocardiograph is attached to a driver. When the driver gets drowsy during driving, the driver pushes a logger button for time recording to record a time when drowsiness has occurred. Then, a correlation between the recorded time and a time when a warning is given is verified.

By a technique such as that described above, data of 133 hours in total for 60 cases with not less than 40 minutes is obtained from 24 drivers.

Of the 60 cases, there are 28 drowsiness reports. The dozing prevention device used for the verification is able to detect drowsiness and give a warning in 20 of the 28 reports (71%). In addition, dozing at the wheel does not occur.

The frequency of giving a warning when there is no drowsiness report is on an average of about once in 73 minutes, and the drivers give their impressions that the frequency of a warning given by erroneous detection is not at an annoying level.

As described above, using the dozing prevention device according to the present invention, in the 60 cases, a pre-dozing state where a driver is about to go into a dozing state can be detected in 71% while erroneous detection is suppressed to a "not annoying" level. Hence, according to the dozing prevention method and the dozing prevention device according to the present invention, before going into a dozing state, human drowsiness is relieved and thus dozing can be prevented, and erroneous detection can be reduced.

Note that the dozing prevention method and the dozing prevention device can also be used for other applications than automobiles.

This application claims priority to Japanese Patent Application No. 2013-041267 filed on Mar. 1, 2013, the entire contents of which are incorporated by reference herein.

INDUSTRIAL APPLICABILITY

A dozing prevention method and a dozing prevention device of the present invention can be widely used for when driving a vehicle such as an automobile, etc.

DESCRIPTION OF REFERENCE SIGNS 1 to 5 Dozing prevention device
10 Electrocardiograph
11 Analyzer
12 Electrocardiogram measurement part
13 RRI calculation part
14 Receiving part
15 Decision part
16 Warning part
17 Interval comparison part
18 Consecutiveness decision part
20 Analyzer
21 Decision part
22 Total-amount-of-change decision part
30 Analyzer
31 Decision part
32 Abnormal value detection part
33 Abnormal value removal part
40 Analyzer
41 Decision part
42 Abnormal value detection part
43 Abnormal value removal part
50 Analyzer
51 Decision part

The invention claimed is:

1. A method for preventing dozing off, comprising the steps of:
 a measurement step measuring human heartbeats;
 a decision step generating a trigger, hereinafter referred to as a "drowsiness trigger", for indicating occurrence of drowsiness when a state in which a time interval between adjacent heartbeats, hereinafter referred to as a "heartbeat interval", is longer than the previous heartbeat interval consecutively occurs; and
 a warning step giving a warning to prevent dozing off when the drowsiness trigger is generated.

2. The method according to claim 1, wherein in the decision step, the drowsiness trigger is generated when the state in which the heartbeat interval is longer consecutively occurs not less than four times.

3. The method according to claim 2, wherein
 in the decision step, the drowsiness trigger is generated when the state in which the heartbeat interval is longer consecutively occurs and a difference between the first heartbeat interval and the last heartbeat interval in the heartbeat intervals consecutively occurring not less than four times exceeds a predetermined time.

4. The method according to claim 3, wherein
 the predetermined time is not less than 60 ms.

5. The method according to claim 1, wherein
 a R-R interval which is an interval between R waves in an electrocardiographic signal is used as the heartbeat interval.

6. The method according to claim 2, wherein
 a R-R interval which is an interval between R waves in an electrocardiographic signal is used as the heartbeat interval.

7. The method according to claim 1, wherein
 in the decision step, the heartbeat interval is considered to have an abnormal value when the heartbeat interval is out of a predetermined range, the abnormal value is eliminated from a target of decision made as to whether a state in which an heartbeat interval is longer has occurred.

8. The method according to claim 3, wherein
 in the decision step, the heartbeat interval is considered to have an abnormal value when the heartbeat interval is out of a predetermined range, the abnormal value is eliminated from a target of decision made as to whether a state in which an heartbeat interval is longer has occurred.

9. The method according to claim 7, wherein
 the predetermined range is 200 ms to 3000 ms.

10. The method according to claim 8, wherein
 the predetermined range is 200 ms to 3000 ms.

11. The method according to claim 7, wherein
 in the decision step, an instantaneous heart rate is calculated by multiplying an inverse of the heartbeat interval, units of seconds, by 60,
 an average of instantaneous heart rates at a plurality of recent points where an absolute value of the difference between the instantaneous heart rate and the previous instantaneous heart rate is not more than a first predetermined number is calculated,
 the heartbeat interval is considered to have an abnormal value when an absolute value of the difference between the average and an instantaneous heart rate corresponding to an heartbeat which is an evaluation target is not less than a second predetermined number, and the abnormal value is eliminated from a target of decision made as to whether a state in which an heartbeat interval is longer has occurred.

12. The method according to claim 8, wherein
 in the decision step, an instantaneous heart rate is calculated by multiplying an inverse of the heartbeat interval, units of seconds, by 60,
 an average of instantaneous heart rates at a plurality of recent points where an absolute value of the difference between the instantaneous heart rate and the previous instantaneous heart rate is not more than a first predetermined number is calculated,
 the heartbeat interval is considered to have an abnormal value when an absolute value of the difference between the average and an instantaneous heart rate corresponding to an heartbeat which is an evaluation target is not less than a second predetermined number, and the abnormal value is eliminated from a target of decision made as to whether a state in which an heartbeat interval is longer has occurred.

13. The method according to claim 11, wherein
 the first predetermined number is 30,
 the second predetermined number is 50,
 the number of a plurality of recent points is from 4 to 20.

14. The method according to claim 1, wherein
 in the decision step, an instantaneous heart rate is calculated by multiplying an inverse of the heartbeat interval, units of seconds, by 60,
 an average of instantaneous heart rates at a plurality of recent points where an absolute value of the difference between the instantaneous heart rate and the previous instantaneous heart rate is not more than a first predetermined number is calculated, the heartbeat interval is considered to have an abnormal value when an absolute value of the difference between the average and an instantaneous heart rate corresponding to an heartbeat which is an evaluation target is not less than a second predetermined number, and the abnormal value is eliminated from a target of decision made as to whether a state in which an heartbeat interval is longer has occurred.

15. The method according to claim 3, wherein
in the decision step, an instantaneous heart rate is calculated by multiplying an inverse of the heartbeat interval, units of seconds, by 60,
an average of instantaneous heart rates at a plurality of recent points where an absolute value of the difference between the instantaneous heart rate and the previous instantaneous heart rate is not more than a first predetermined number is calculated,
the heartbeat interval is considered to have an abnormal value when an absolute value of the difference between the average and an instantaneous heart rate corresponding to an heartbeat which is an evaluation target is not less than a second predetermined number, and the abnormal value is eliminated from a target of decision made as to whether a state in which an heartbeat interval is longer has occurred.

16. The method according to claim 14, wherein
the first predetermined number is 30,
the second predetermined number is 50,
the number of a plurality of recent points is from 4 to 20.

17. A dozing prevention device wherein the device accepts a time interval between adjacent heartbeats, hereinafter referred to as a "heartbeat interval"; decides that drowsiness has occurred when a state in which the heartbeat interval is longer than the previous heartbeat interval consecutively occurs; and gives a warning to prevent dozing off.

18. The dozing prevention device according to claim 17, further including:
a measurement part for measuring human heartbeats; and
a signal processing part for generating a heartbeat interval based on the measured human heartbeats.

19. The dozing prevention device according to claim 17, wherein
a R-R interval which is an interval between R waves in an electrocardiographic signal is used as the heartbeat interval.

20. The dozing prevention device according to claim 18, wherein
a R-R interval which is an interval between R waves in an electrocardiographic signal is used as the heartbeat interval.

* * * * *